United States Patent [19]
Yan et al.

[11] Patent Number: 5,961,956
[45] Date of Patent: Oct. 5, 1999

[54] FROZEN ULTRASONIC GAS SUSPENSIONS

[75] Inventors: Feng Yan, Geneva; Michel Schneider, Troinex, both of Switzerland; Jean Brochot, Feigeres, France

[73] Assignee: Bracco Research S.A., Switzerland

[21] Appl. No.: 08/944,408

[22] Filed: Oct. 6, 1997

Related U.S. Application Data

[63] Continuation of application No. 08/573,540, Dec. 15, 1995, abandoned.

[30] Foreign Application Priority Data

Dec. 16, 1994 [EP] European Pat. Off. ............. 94810731

[51] Int. Cl.$^6$ ......................... A61K 49/04; A61K 9/127; A61K 9/14
[52] U.S. Cl. ........................ 424/9.52; 424/9.51; 424/450; 424/489
[58] Field of Search ................. 424/9.52, 9.51, 424/9.5, 489, 450, 490, 497, 501, 502; 264/4, 4.1, 4.3, 5; 427/213.31, 212, 213.35, 213.36; 428/402, 402.2

[56] References Cited

U.S. PATENT DOCUMENTS

| | | | |
|---|---|---|---|
| 4,276,885 | 7/1981 | Tickner et al. ........................ | 128/660 |
| 4,347,707 | 9/1982 | Zemelman et al. . | |
| 5,205,287 | 4/1993 | Erbel et al. ............................ | 128/632 |
| 5,271,961 | 12/1993 | Mathiowitz et al. .............. | 427/213.31 |
| 5,518,709 | 5/1996 | Sutton et al. .......................... | 424/9.52 |
| 5,529,766 | 6/1996 | Klaveness et al. .................... | 424/9.52 |

FOREIGN PATENT DOCUMENTS 1467900 1/1969 Germany .

OTHER PUBLICATIONS

*Journal of Liposome Research*, pp. 861–874 (1994); Unger et al; "Gas Filled Lipid Bilayers as Imaging Contrast Agents".

*Primary Examiner*—Jose' G. Dees
*Assistant Examiner*—Michael G. Hartley
*Attorney, Agent, or Firm*—Nixon & Vanderhye

[57] ABSTRACT

Disclosed are suspensions of gas microbubbles immobilised within a frozen aqueous carrier liquid comprising usual additives and stabilisers, in which the carrier liquid is a physiologically acceptable, the immobilised gas microbubbles are microbubbles bound by an evanescent envelope or a tangible membrane. The suspensions, when in liquid form, are injectable and useful as a contrast agents in ultrasonic imaging of blood pool and tissue of living beings. The gas microbubbles are immobilised within the carrier by freezing a suspension of microbubbles with average sizes below 50 μm, preferably below 10 μm and more preferably between 2 μm and 8 μm, to a temperature between −1° C. and −76° C. and maintaining this temperature for prolonged periods of time. The microbubbles may be stabilised by a surfactant such as a lamellar phospholipid or may comprise a membrane made of synthetic or natural polymer or protein. A method of cold storage of microbubble suspensions as well as their use is also disclosed.

21 Claims, 6 Drawing Sheets

FROZEN ULTRASONIC GAS SUSPENSIONS

This is a rule 62 file wrapper continuation of application Ser. No. 08/573,540, filed Dec. 15, 1995, now abandoned.

TECHNICAL FIELD

The invention relates to suspensions of gas bubbles immobilised within a frozen aqueous carrier medium. The invention also concerns a method of cold storage of the gas bubble suspensions and their use as contrast agents for ultrasonic imaging of human and animal body.

BACKGROUND ART

Rapid development of ultrasound contrast agents in the recent years has generated a number of different formulations which are useful in ultrasound imaging of organs and tissue of human or animal body. These agents are designed to be used primarily as intravenous or intra-arterial injectables in conjunction with the use of medical echographic equipment. These instruments typically group B-mode image formation (based on the spatial distribution of backscatter tissue properties) and Doppler signal processing (based on Continuous Wave or pulsed Doppler processing of ultrasonic echoes to determine blood or liquid flow parameters). Other ultrasound imaging methods could also benefit from these agents in the future, such as Ultrasound Computed Tomography (measuring attenuation in transmission), or Diffraction Computed Tomography (measuring scattering and attenuation parameters in angular reflection). Based on suspensions of gas microbubbles in aqueous liquid carriers, these injectable formulations may basically be divided into two categories: Aqueous suspensions in which the gas microbubbles are bounded by the gas/liquid interface, or an evanescent envelope involving the molecules of the liquid and a surfactant loosely bound at the gas to liquid interface and suspensions in which the microbubbles have a material boundary or a tangible envelope formed of natural or synthetic polymers. In the latter case the microbubbles are referred to as microballoons. There is yet another kind of ultrasound contrast agents: suspensions of porous particles of polymers or other solids which carry gas microbubbles entrapped within the pores of the microparticles. These contrast agents are considered here as a variant of the microballoon kind. Although physically different, both kinds of gas microbubbles when in suspension are useful as ultrasonic contrast agents. More on these different formulations may be found in EP-A-0 077 752 (Schering), EP-A-0 123 235 (Schering), EP-A-0 324 938 (Widder et al.), EP-A-0 474 833 (Schneider et al.), EP-A-0 458 745 (Bichon et al.), U.S. Pat. No. 4,900,540 (Ryan), U.S. Pat. No. 5,230,882 (Unger), etc.

Certain of the above mentioned ultrasound contrast agents are developed and commercially available, while others are at different stages of clinical trials. However, whether commercially available or on clinical tests, these products all suffer from problems linked with storage. The problems of storage are intrinsic to suspensions which, due to their very nature, undergo phase separation or segregation, gas bubble aggregation, gas diffusion and, after long periods, even precipitation of various additives. Segregation of the gas microbubbles or microballoons comes from the fact that the suspensions are typically made of uncalibrated microbubbles whose sizes vary from about 1 $\mu$m up to about 50 $\mu$m. A vast majority of the gas bubbles in the known suspensions is found to be between 1 $\mu$m and about 10 $\mu$m. Due to the microbubble size distribution, these suspensions, during storage, undergo segregation in which larger microbubbles migrate to the top while the smaller ones concentrate in the lower parts, often leading to complete phase separation. Attempts to resolve this problem through the use of viscosity enhancing agents have shown that the rate of segregation may be reduced but not eliminated.

Gas microbubble aggregation is a process during which the larger bubbles absorb the smaller ones, thus growing in size. With phase separation, this process accelerates and suspensions with microbubbles having average size of e.g. between 2 $\mu$m and 8 $\mu$m after a while may evolve in suspensions with microbubble size between e.g. 5 $\mu$m to 12 $\mu$m or larger. This is particularly undesirable in cases where suspensions of calibrated microbubbles and suspensions intended for opacification of the left heart are concerned. The change in size does not only alter the echogenic properties of the contrast agent, but also renders the agent inapplicable for certain applications such as those based on the passage of the microbubbles through the lungs. Microbubbles with sizes over 10 $\mu$m are unlikely to pass through the lung capillaries and therefore, in addition to creating hazardous conditions such suspensions are less suitable for imaging of the left heart.

Another problem with gas suspensions and their storage comes from the gas diffusion which occurs at relatively low rates, but which accelerates with phase separation. Inevitable escape of the gas from the microbubble suspensions is thus further aggravated and in extreme cases may lead to complete gas depletion of the medium. Hence, the combined effect of these various mechanisms on destruction of the gas suspensions therefore results in a very rapid degradation of the agent.

In some ultrasound imaging approaches, one of the desirable aspects of these contrast agents is for the microbubbles or gas-containing particles to be distributed within a tight size window. The reason is given hereafter. The effectiveness of these agents to increase the contrast in images produced by medical ultrasonographic equipment is based, primarily, on greatly enhanced scattering of the incoming ultrasonic energy, and secondly, on modified attenuation properties of the tissues containing these agents. By contrast, it is meant a measure of the relative signal amplitude obtained from regions to be perfused by the contrast agent compared with the signal amplitude from regions not receiving the contrast agent. By enhancement, it is meant an increase in the contrast value observed following administration of the contrast agent, compared to the contrast observed prior administration. As mentioned earlier, the type of imaging equipment most directly benefitting from these agents is the family of echographic instruments (B-mode or Doppler). The different attenuation properties of tissues containing the agent compared to those not containing the agent can also be exploited to improve the diagnostic value of the imaging procedure. Furthermore, the ultrasonic-frequency dependence of both the scattering and attenuation properties of the agent can be exploited to increase spatial tissue discrimination further. In these cases, the physical laws governing this frequency dependence systematically depend on the microbubble- or particle-size. Thus, the algorithms used are more efficient when acting on echoes originating from microbubbles or particles with tight size-distribution. As an example, one such approach exploits non-linear oscillation of microbubbles to detect echo frequency-components at the second-harmonic of the fundamental excitation frequency. Since the tissues not containing the contrast agent do not exhibit the same non-linear behaviour as the microbubbles, this method is able to enhance significantly the contrast between the regions containing and those not containing the contrast agent. This enhancement is more pronounced, for a given particle-count per unit volume, when the sizes are narrowly distributed. However, the preparation of products with such narrow-size distributions is time consuming; providing a ready supply of these calibrated suspensions would facilitate greatly the further development and use of this technique. Reliable storage of such preparations with unchanged size distributions is thus also of great interest.

Further difficulties with storage of aqueous gas suspensions is experienced with ultrasound contrast agents which contain phospholipids as stabilisers of the gas microbubbles. Due to hydrolysis of phospholipids, the concentration of the stabilizer (surfactant), during storage, is constantly diminished, causing loss of the microbubble content and degradation of echogenic properties of the suspension. Thus so far the problem of storage of ultrasound contrast agents comprising gas microbubble suspensions remains open.

Cold storage of aqueous gas suspensions by freezing has been known for quite some time in the food industry. For example, U.S. Pat. No. 4,347,707 (General Foods Corp.) discloses storage of gasified ice with high gas content and good storage stability by a method in which the gasified ice is prepared by contacting an aqueous liquid with hydrate-forming gases under pressure and at a temperature such that the gas hydrate complex suspended in the liquid is formed and the temperature and pressure are controllably lowered to produce e.g. carbonated ice with 85–110 ml of $CO_2$/g. According to the document, the gasified ice has high gas content, prolonged storage stability, is suitable for commercial distribution in the frozen state and, when placed in water, provides vigorous effervescence.

It follows that freezing of the gas suspensions in order to store them for prolonged periods of time, and reuse the preserved suspensions when necessary would not be suitable for ultrasonic contrast agents because the suspended gas has a tendency to escape from the carrier medium during defrosting. Further difficulty with the frozen gas suspensions of microbubbles lies in the fact that the expansion of the carrier medium during the freezing creates internal forces which simply destroy or crush the microbubble envelope liberating the entrapped gas and letting it escape either during storage or later during defrosting of the suspension. This problem is particularly severe for the suspensions of microbubbles having material or tangible envelopes.

SUMMARY OF THE INVENTION

Briefly summarised, the invention relates to frozen suspensions of gas bubbles immobilised within a frozen aqueous carrier medium in which the carrier medium comprising the gas bubbles with usual additives is a physiologically acceptable carrier. The immobilised gas bubbles are microbubbles bound by an evanescent envelope or a tangible membrane and the suspensions, when in liquid form, are injectable into living beings and are useful as a contrast agents for ultrasonic imaging of the blood pool and tissue of human and animal patients.

According to the invention, the temperatures of the frozen suspensions are between $-1°$ C. and $-196°$ C., preferably between $-10°$ C. and $-76°$ C. while the size of the gas microbubbles is below 50 $\mu$m and preferably below 10 $\mu$m. Particularly useful are suspensions in which the size of the microbubbles is between 2 $\mu$m and 9 $\mu$m, while the suspensions of microbubbles with size between 3 $\mu$m and 5 $\mu$m are even more useful.

In view of the difference in biodegradability between the suspensions comprising gas microballoons or microbubbles with a tangible envelope in which the membrane is made of synthetic or natural polymer or protein, and the suspensions comprising gas microbubbles with evanescent envelopes, the frozen suspensions of the latter would be more advantageous, particularly when lamellar phospholipids in the form of mono- or pluri-molecular membrane layers are used.

The invention also relates to a method of storing microbubble suspensions in which the suspension is placed into a cooling device, microbubbles are immobilised within the carrier medium by cooling to a temperature below the freezing point of the suspension, preferably a temperature between $-1°$ C. and $-196°$ C., and more preferably between $-10°$ C. and $-76°$ C., and the freezing conditions are maintained for prolonged periods of time. Optionally, the frozen suspension may be kept in an atmosphere of an inert gas or a mixture of gases, at least one of which is the gas encapsulated in the microbubbles. The gas is preferably selected from halogen containing gases, air, oxygen, nitrogen, carbon dioxide or mixtures thereof.

Use of injectable suspensions of the invention for ultrasonic echography imaging of organs and tissue and the manufacture of ultrasound contrast agents is also disclosed.

DETAILED DESCRIPTION OF THE INVENTION

According to the invention, there is provided a frozen suspension of gas microbubbles in which the microbubbles are immobilised within a frozen aqueous carrier medium which in addition to the microbubbles includes usual additives. The aqueous carrier is physiologically acceptable and the suspension, when in a liquid form is injectable into living beings and is useful as an ultrasound contrast agent for imaging of blood pool and tissue of human and animal patients. The immobilised gas microbubbles bound by an evanescent envelope or a tangible membrane are entrapped between molecules of the frozen carrier medium whose temperature is between $-1°$ C. and $-196°$ C., preferably between $-10°$ C. and $-76°$ C. The exact temperature range used will depend on the choice of gas in the microbubbles but also on the kind and quantity of additives used. Thus, for example, in the case of air or nitrogen, the temperature may be anywhere between −1° C. and −196° C., while, in the case of $C_4F_8$, the temperature will be between −1° C. and −5° C. When polyoxypropylene/polyoxyethylene copolymers or polyethylene glycol are used as additives depending on the total amount present in the suspension the highest acceptable temperature may be −5° C. or even −10° C. instead of −1° C.

The size of most of the microbubbles in the suspension is typically below 50 μm, but for intravenously injectable contrast agents the microbubble size will be preferably below 10 μm.

For most applications the suspensions with microbubbles having the size distribution between 2 μm and 9 μm would satisfy the requirements, however, when dealing with suspensions of calibrated microbubbles the sizes may be anywhere in that range. For example, between 2–4 μm, 3–5 μm, 4–6 μm, 5–7 μm, 6–8 μm, 7–9 μm however the microbubble with the size range between 3 μm and 5 μm is preferred.

Figure 5A:
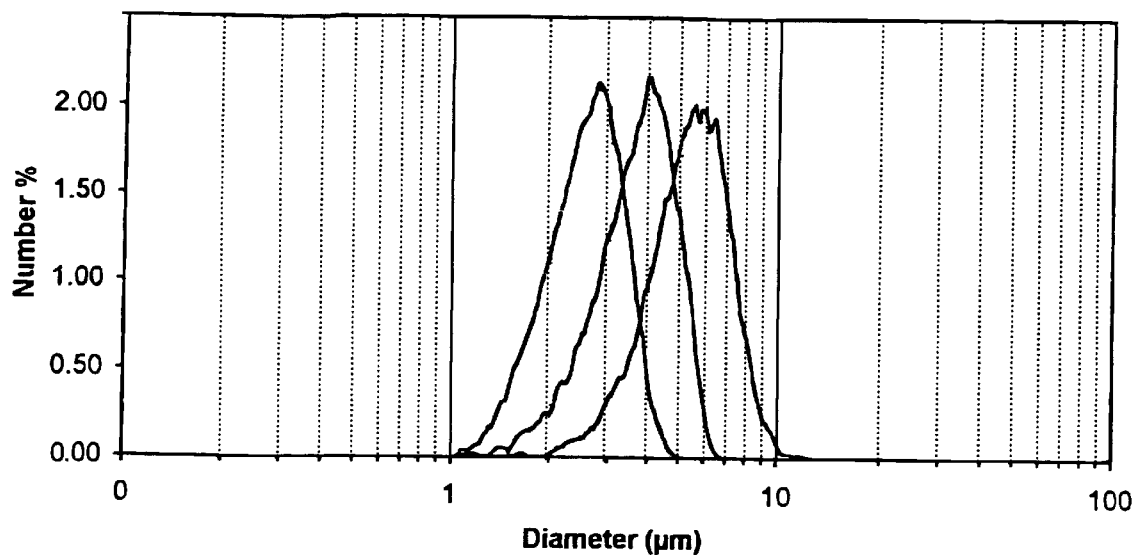
FIG. 5 is a diagram showing the microbubble size distribution in number (FIG. 5A) and gas volume (FIG. 5B) of calibrated microbubbles with average size of 3 $\mu$m, 4 $\mu$m and 6 $\mu$m.
Figure 5B:
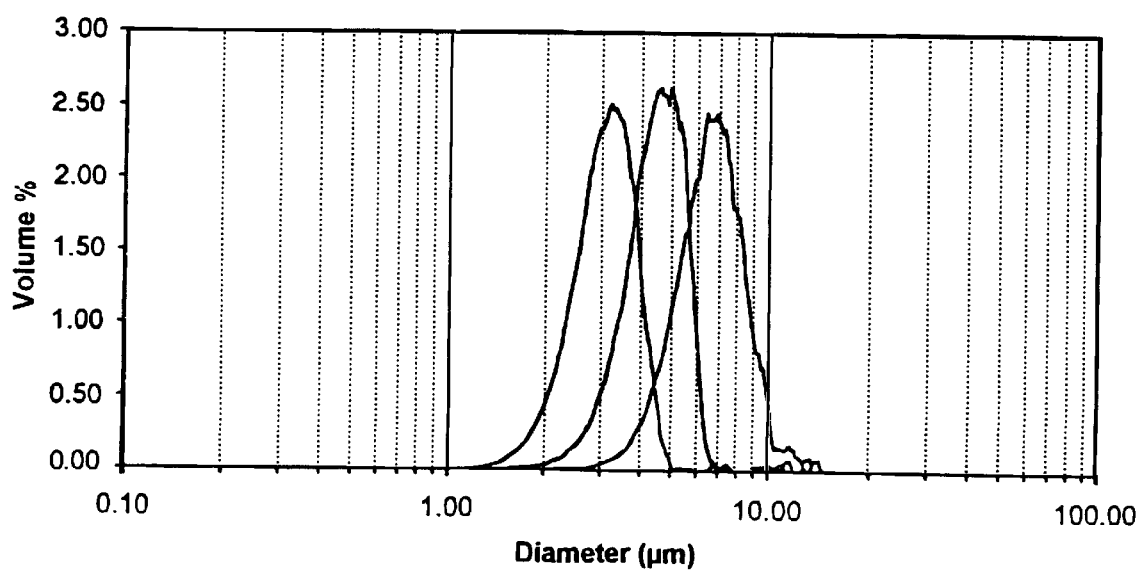
Figure 6A:
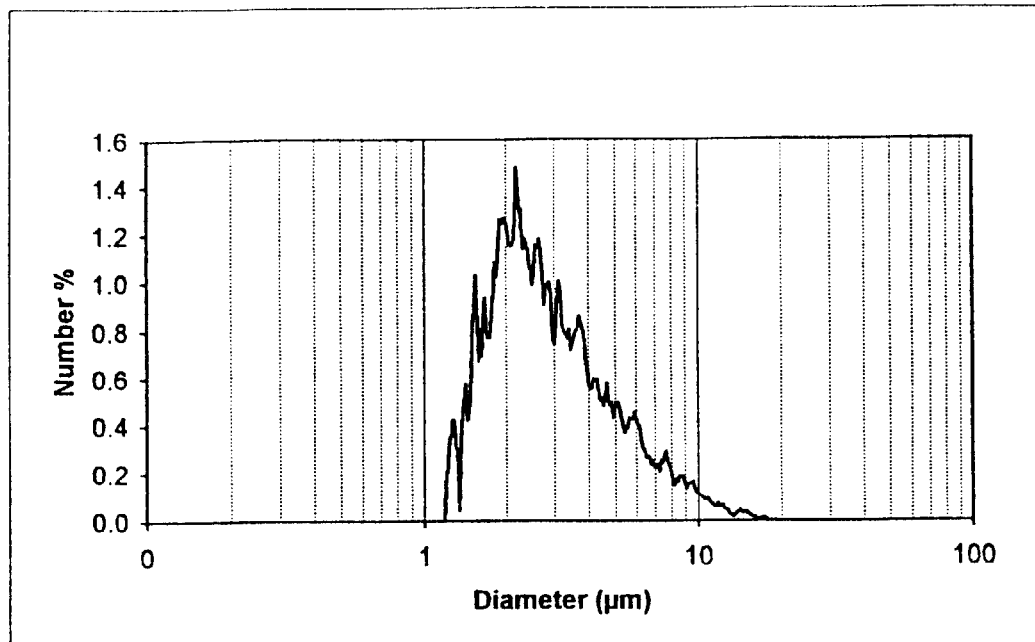
FIG. 6 is a diagram showing the microbubble size distibution in number (FIG. 6A) and gas volume (FIG. 6B) for a sample of non-calibrated microbubbles.
Figure 6B:
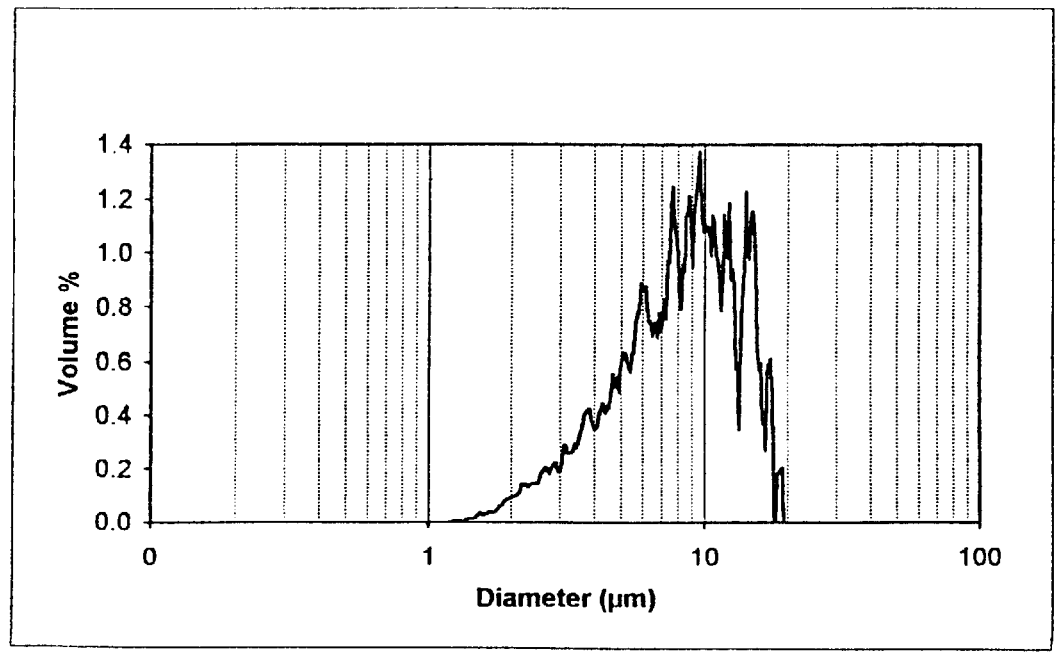

Thus the invention also provides frozen suspensions of microbubbles with a very narrow size distribution. Typical microbubble size distributions of suspensions of calibrated microbubbles will be as those illustrated in FIG. 5. where the distributions are given in terms of the microbubble number distribution (as determined by Coulter counter) FIG. 5A and in terms of the microbubble volume distribution (as determined by Coulter counter) FIG. 5B. In contrast to suspensions containing calibrated microbubbles, the suspensions containing non-calibrated gas bubbles will have typically the number and the volume size distribution patterns similar to those shown in FIGS. 6A & 6B. From these figures it is readily appreciated that the echographic responses suspensions made from calibrated gas microbubbles will be more uniform, will provide less scatter and consequently sharper images than the suspensions with non-calibrated microbubbles. As already mentioned these calibrated suspensions are very desirable but their use so far was very limited. Thus these desirable suspensions are now readily available through a simple conversion of frozen suspensions which may be stored at low temperatures for prolonged periods of time without undue loss of their initial echogenicity.

A further advantage of the invention comes from the fact that in order to generate echo-signal components at twice the fundamental frequency, second harmonic imaging requires non-linear oscillation of the contrast agent. Such behaviour imposes the ultrasound excitation level to exceed a certain acoustic threshold at a certain depth in tissue. During non-linear oscillation, a frequency conversion takes place, causing conversion of the acoustic energy from the fundamental excitation frequency up to its second harmonic. Thus significant energies transmitted to the microbubbles during this type of imaging require microbubbles sufficiently resistant to survive these conditions. The invention provides for an easy and convenient access to suspensions of having microbubbles with good resistance to pressure variations as they can now be prepared in advance, stored and used when needed.

As already mentioned, in addition to the gas microbubbles, the frozen suspensions of the invention contain additives which include various surfactants, viscosity enhancing agents, stabilisers, etc. Surfactants which may include film forming and non-film forming surfactants include phospholipids in lamellar or laminar form which are known to stabilise the microbubble evanescent gas/liquid envelope. The lamellar phospholipids may be a in the form of mono- or pluri-molecular membrane layers or liposomes.

Depending on the type of microbubbles, i.e. with evanescent envelope or a tangible membrane the carrier medium may include as additives hydrating agents and/or hydrophilic stabiliser compounds such as polyethylene glycol, carbohydrates such as galactose, lactose or sucrose, dextran, starch, and other polysaccharides or other conventional additives like polyoxypropylene glycol and polyoxyethylene glycol and their copolymers; ethers of fatty alcohols with polyoxyalkylene glycols; esters of fatty acids with polyoxyalkylated sorbitan; soaps; glycerol-polyalkylene stearate; glycerol-polyoxyethylene ricinoleate; homo- and copolymers of polyalkylene glycols; polyethoxylated soya-oil and castor oil as well as hydrogenated derivatives; ethers and esters of sucrose or other carbohydrates with fatty acids, fatty alcohols, these being optionally polyoxyakylated; mono-, di- and triglycerides of saturated or unsaturated fatty acids; glycerides of soya-oil and sucrose may also be used. Surfactants may be film forming and non-film forming and may include polymerizable amphiphilic compounds of the type of linoleyl-lecithins or polyethylene dodecanoate. Preferably, the surfactants are film forming and more preferably are phospholipids selected from phosphatidic acid, phosphatidylcholine, phosphatidylethanolamine, phosphatidylserine, phosphatidylglycerol phosphatidylinositol, cardiolipin, sphingomyelin and mixtures thereof. In addition to the film forming surfactants mentioned, the suspensions may further include up to 50% by weight of non-laminar surfactants selected from fatty acids, esters and ethers of fatty acids and alcohols with polyols such as polyalkylene glycols, polyalkylenated sugars and other carbohydrates, and polyalkylenated glycerol. Particularly suitable substances include dicetylphosphate, cholesterol, ergosterol, phytosterol, sitosterol, lanosterol, tocopherol, propyl gallate, ascorbyl palmitate and butylated hydroxytoluene.

It is understood that the invention is not limited only to the suspensions of gas microbubbles with an evanescent envelope. Any suitable particles filled with gases such as porous particles, liposomes or microballoons having an envelope produced from phospholipids, synthetic or natural polymers or proteins may conveniently be used. Thus it has been established that microballoons prepared with albumin, or liposome vesicles can be successfully stored for prolonged periods of time in the frozen state. Defrosted suspensions containing these microballoons have demonstrated acceptable echogenicities showing a relatively small microbubble loss. Suspensions in which the microbubbles were stabilised with sorbitol or non-ionic surfactants such as polyoxyethylene/polyoxy-propylene copolymers (commercially known as Pluronic®) have demonstrated equally good imaging capability after storage.

The additives used for the suspensions of the invention may further include viscosity enhancers and/or stabilisers selected from linear and cross-linked poly- and oligo-saccharides, sugars, hydrophilic polymers and iodinated compounds. In such case the weight ratio of these compounds to the surfactants comprised is between about 1:5 to 100:1.

The suspensions according to the invention and prepared with different gases or gas mixtures usually contain $10^7$–$10^8$ microbubbles/ml, $10^8$–$10^9$ microbubbles/ml or $10^9$–$10^{10}$ microbubbles/ml. These concentrations remain virtually the same after prolonged storage, i.e. several months, and if suspensions are made with $SF_6$, $C_3F_8$ or their mixtures or mixtures of air with $SF_6$ or $C_5F_{12}$ they do not change even after repeated freeze and thaw cycles.

When the microbubbles in the suspension have a tangible membrane, the membrane is made of synthetic or natural polymer or protein. The polymer which constitutes the envelope or bounding membrane of the injectable microballoons can be selected from most hydrophilic, biodegradable physiologically compatible polymers. Among such polymers one can cite polysaccharides of low water solubility, polylactides and polyglycolides and their copolymers, copolymers of lactides and lactones such as ε-caprolactone, ∂-valerolactone and polypeptides. The great versatility in the selection of synthetic polymers is here of advantage since, as with allergic patients, one may wish to avoid using microballoons made of natural proteins (albumin, gelatin). Other suitable polymers include poly-(ortho)esters, copolymers of lactic and glycolic acid, poly(DL-lactide-co-∂-caprolactone), poly(DL-lactide-co-∂-valerolactone), poly (DL-lactide-co-g-butyrolactone), polyalkyl-cyanoacrylates; polyamides, polyhydroxybutyrate; polydioxanone; poly-β-aminoketones, polyphosphazenes and polyanhydrides. Polyamino-acids such as polyglutamic and polyaspartic acids can also be used as well as their derivatives, i.e. partial esters with lower alcohols or glycols. One useful example of such polymers is poly-(tert-butylglutamate).

When the membrane is made from proteinaceous material the protein is albumin.

Although in conjunction with suitable surfactants and stabilisers, halogen containing gases, air, oxygen, nitrogen or carbon dioxide may be used alone, recently, use of mixtures of the halogen containing gases with air, oxygen, nitrogen and carbon dioxide has also been proposed. The halogen containing gases are gases selected from sulphur hexafluoride, tetrafluoromethane, chlorotrifluoromethane, dichlorodifluoromethane, bromotrifluoromethane, bromochlorodifluoromethane, dibromodifluoromethane dichlorotetrafluoroethane, chloropentafluoroethane, hexafluoroethane, hexafluoropropylene, octafluoropropane, hexafluorobutadiene, octafluoro-2-butene, octafluorocyclobutane, decafluorobutane, perfluorocyclopentane, dodecafluoropentane or mixtures of thereof and preferably sulfur hexafluoride, tetrafluoromethane, hexafluoroethane, hexafluoropropylene, octafluoropropane, hexafluorobutadiene, octafluoro-2-butene, octafluorocyclobutane, decafluorobutane, perfluorocyclopentane, dodecafluoropentane.

The invention also relates to a method of storing microbubble suspensions in which the suspension is placed into a cooling device such as a refrigerator, microbubbles are immobilised within the carrier medium by cooling to a temperature below the freezing point of the suspension, preferably a temperature between $-1°$ C. and $-196°$ C., and more preferably between $-10°$ C. and $-76°$ C. the freezing conditions are maintained for prolonged periods of time. Optionally, the frozen suspension is kept in an atmosphere of an inert gas or a mixture of gases at least one of which is the gas encapsulated in the microbubbles. The gas is preferably selected from halogen containing gases, air, oxygen, nitrogen, carbon dioxide or mixtures thereof.

It has been established that gases or gas mixtures used for the frozen suspension of the invention should have boiling points which are below $-18°$ C. This means that suspensions made with halogenated gases such as $C_4F_8$ and $C_5F_{10}$ alone will have very poor storage stability and will lose practically all of their echogenicity after freezing. This was particularly surprising since all other halogenated gases produced very stable frozen suspensions which survived several freeze/thaw cycles without significant loss of echogenicity. Even "doping" these gases with small amounts of other halogenated gases or even vapours of halogenated substance which at room temperatures are liquids such as $C_5F_{12}$ has produced mixtures which could not be stored frozen. On the other hand, admixing air with certain quantities of these gases have produced suspensions which have had very good storage stability and very good echogenicity after several freeze/thaw cycles.

As mentioned above, when in a liquid state, the injectable suspensions of the invention are useful as contrast agents for ultrasonic imaging of organs and tissue. Clearly, prior to use, the suspensions are defrosted and optionally maintained at room temperature for a period of time and then administered to the patient. The patient is then scanned with an ultrasonic probe and an image of the scanned region is produced.

Also within the scope of the invention is a method of the manufacture of ultrasound echographic contrast agents from the frozen injectable suspensions of the invention. By the manufacture it is meant that fairly concentrated suspensions (e.g. $10^{10}$–$10^{11}$ microbubbles/ml or more) of calibrated or uncalibrated microbubbles are stored in a frozen state for a period of time and when needed defrosted suspensions are, optionally, diluted to the desired concentration by addition of the same or a different physiologically acceptable liquid carrier. It is also envisaged that at this point further additives or conditioners may be added.

The invention is further illustrated by the following examples:

EXAMPLE 1

Fifty eight milligrams of diarachidoylphosphatidylcholine (DAPC), 2.4 mg of dipalmitoylphosphatidic acid (DPPA) both from Avanti Polar Lipids (USA) and 3.94 g of polyethyleneglycol (PEG 4000 from Siegfried) were dissolved at 60° C. in tert-butanol (20 ml) in a round bottom glass vessel. The clear solution was rapidly cooled at $-45°$ C. and lyophilised. Aliquots (25 mg) of the white cake obtained were introduced in 10 ml glass vials. The vials were closed with rubber stoppers, evacuated, and filled with selected gases or gas mixtures (see Table 1). Saline (0.9% NaCl) was then injected through the stoppers (5 ml per vial) and the lyophilisates were dissolved by vigorous shaking.

The microbubble suspensions were introduced in a cold storage room ($-18°$ C). Three days later they were thawed at room temperature (23° C.) and analysed with regard to bubble concentration (by using a Coulter Multisizer) and absorbance at 700 nm of a 1/50 dilution. The absorbance at 700 nm is a measure of the overall turbidity of the bubble suspension.

TABLE 1

| Gas or gas mixture | Boiling point (° C.) | Water solubility* | Absorbance (% of initial) | Bubbles recovered (%) |
| --- | --- | --- | --- | --- |
| air | −195 | 0.0167 | 33 | 14 |
| SF6 | −63.8 | 0.005 | 57 | 23 |
| $C_3F_8$ | −36.7 | <<0.005 | 59 | 54 |
| $C_4F_8$ | −6 | 0.016 | 11 | 8 |
| $C_4F_{10}$ | −1.7 | <0.005 | 7 | 4 |
| air (+5% C5F12) | −195 | 0.0167 | 71 | 49 |
| air (+10% C5F12) | −195 | 0.0167 | 55 | 34 |
| air (+10% C4F8) | −195 | 0.0167 | 50 | 30 |
| air (+10% C4F10) | −195 | 0.016 | 52 | 32 |
| SF6 (+5% C5F12) | −63.8 | 0.005 | 62 | 41 |
| $C_3F_8$ (+5% C5F12) | −36.7 | <<0.005 | 84 | 71 |
| $C_4F_8$ (+5% C5F12) | −6 | 0.016 | 7 | 6 |

TABLE 1-continued

| Gas or gas mixture | Boiling point (° C.) | Water solubility* | Absorbance (% of initial) | Bubbles recovered (%) |
|---|---|---|---|---|
| $C_4F_{10}$ (+5% C5F12) | −1.7 | <0.005 | 1 | 1 |
| Xenon (+5% C5F12) | −108.1 | 0.108 | 38 | 17 |

*expressed as Bunsen coefficient

Results given in Table 1 show that the stability to freezing depends on the boiling point and the water solubility of the gas. Less bubbles are recovered in the case of gases with boiling points above −18° C. With regard to the gases with boiling points below −18° C., the lower the solubility in water the higher the recovery of bubbles. It is also interesting to note that the addition of a small amount of a high molecular weight gas with low water solubility such as dodecafluoropentane ($C_5F_{12}$) improves the recovery of bubbles after thawing in the case of gases with low boiling points but not for gases with boiling points above −18° C. Finally, microbubbles filled with $C_4F_8$ and $C_4F_{10}$ on their own or in mixtures with small amounts of dodecafluoropentane have very poor stability to freezing/thawing. However, when these gases are used in combination with air suspensions of microbubbles containing the mixtures show better results in terms of echogenicity or the microbubble loss than the suspensions containing air microbubbles.

EXAMPLE 2

Suspensions of $SF_6$ microbubbles prepared as described in Example 1 were frozen slowly (approx. 30 min) to −18° C. or rapidly (within a minute) to −45° C. Other suspensions of $SF_6$ microbubbles were first kept at room temperature until all bubbles had risen at the surface before freezing. Others were frozen while the bubbles were homogeneously distributed in the solution. The frozen suspensions were stored at −18° C. and −45° C. for one month and then defrosted.

TABLE 2

| Test | Bubble conc. (% of initial) | Bubble volume (% of initial) |
|---|---|---|
| Slow freezing (−18° C.) | 16 | 39 |
| Rapid freezing (−5° C.) | 24 | 51 |
| Decanted (−18° C.) | 14 | 34 |
| Homogeneous (−18° C.) | 24 | 61 |

The results in Table 2 show that the rate of freezing has a relatively small influence on the final result. The recovery in the case of homogeneous suspensions is better than in the case of suspensions of decanted microbubbles.

EXAMPLE 3

Multilamellar liposomes (MLVs) were prepared by dissolving 4.5 g of hydrogenated soy phosphatidylcholine (HSPC from Nattermann) and 0.5 g of dicetylphosphate (Fluka, Switzerland) in chloroform-methanol (2/1), then evaporating the solvents to dryness in a round bottomed flask using a rotary evaporator. The residual lipid film was dried in a vacuum desiccator. After addition of 100 ml of distilled water the suspension was incubated at 70° C. for 30 min under agitation. The liposome suspension was adjusted to a final lipid concentration of 25 mg per ml by addition of distilled water.

An aliquot of the liposome suspension (100 ml) was introduced in a gas tight glass reactor equipped with a high speed mechanical emulsifier (Polytron). The gas phase in the reactor was air containing 5% $C_5F_{12}$ (as determined by density measurement). After homogenisation (10,000 rpm, 1 min) the milky suspension obtained was introduced in a decantation funnel. After 6 hours, a white layer of bubbles could be seen on top of the solution. The lower (liposomes containing) phase was removed, a small amount of fresh water added and the microbubble layer rehomogenised. The procedure (decantation) was repeated and four samples with different microbubble sizes were prepared (see WO94/09829). The samples were frozen at −18° C. and 24 hours later thawed to room temperature.

TABLE 3

| Initial diameter Dn (μm) | Diameter Dn after freeze/thaw | Bubble conc. (% of initial) | Absorbance 700 nm (% of initial) |
|---|---|---|---|
| 2.5 | 2.5 | 19 | 20 |
| 4.6 | 4.5 | 60 | 68 |
| 6.0 | 6.2 | 86 | 100 |
| 7.6 | 8.1 | 76 | 91 |

From the results obtained (Table 3) it seems that the freeze/thaw treatment does not have an influence on the mean microbubble diameter. From the experiments it appears that microbubbles with larger diameter (>2.5 μm) withstand the freeze/thaw treatment better than microbubbles with smaller diameter. It is further observed that in certain cases the rate of defrosting may influence the final concentration of the microbubbles present in the sample. The exact relationship is still unclear, however, there are indications that the loss of microbubbles is inversely proportional to the defrosting rate. Preliminary results indicate that better results in terms of microbubble concentration (count) and the total volume of gas in the suspensions are obtained at accelerated defrosting i.e. defrosting carried our in a water bath at 25° C. than when the samples are left at 5° C. or 20° C. to defrost more gradually. The largest loss of gas volume was observed for samples defrosted at 5° C.

EXAMPLE 4

The experiment described in Example 3 was repeated using a mixture of surfactants instead of MLVs. The surfactant mixture was obtained by dissolving 1 g of dipalmitoylphosphatidylglycerol (DPPG Na salt from Avanti Polar Lipids, USA) and 3 g of Pluronic® $F_{68}$ (a copolymer of polyoxyethylene-polyoxypropylene with a molecular weight of 8400) in distilled water (80 ml). After heating at about 70° C. a clear solution was obtained. This solution was cooled at room temperature and the volume was completed to 100 ml with glycerol. The surfactant solution was introduced in the glass tight reactor equipped with a Polytron emulsifier. After homogenisation (10,000 rpm, 1 min) a milky suspension was obtained with on top a layer of foam. The foam was discarded and the lower phase containing $10^9$ microbubbles per ml was recovered. This phase was left for several hours before collecting the white microbubble layer. The microbubbles collected were rehomogenised in distilled water, decanted a second time and frozen/thawed as described previously. When comparing the characteristics of the bubbles before and after freezing, no significant variation in the total bubble concentration (before $1.3 \times 10^8$ bubbles per ml, after $1.25 \times 10^8$), or the mean diameter Dn (before 4.0 μm, after 3.9) was observed.

EXAMPLE 5

$SF_6$ bubbles were prepared as described in Example 1 and decanted as described in Example 3. During the removal of the lower aqueous phase, an equivalent volume of $SF_6$ gas was introduced in the funnel. The bubble layer was resuspended in distilled water, 0.9% NaCl, 3% aqueous glycerol solution and 100 mg/ml trehalose solution. The bubble concentrations and absorbance at 700 nm (after dilution) was determined prior to and after a freeze-thaw treatment.

The results in Table 4 show an excellent recovery of the bubbles independently of the suspension medium. It is important to note that the microbubble recovery here is between 66 and 96% which may seem in a contradiction with previous results reported in Table 1 & 2. However, in this case, firstly, the microbubbles are calibrated i.e. more stable than uncalibrated ones, and secondly the size on the bubbles used here is above 4 µm.

TABLE 4

| Suspension medium | Absorbance 700 nm (% of initial) | Bubble conc. (% of initial) |
|---|---|---|
| distilled water | 69 | 66 |
| 0.9% NaCl | 86 | 92 |
| 3% glycerol | 92 | 96 |
| 100 mg/ml trehalose | 89 | 73 |

EXAMPLE 6

Decanted $SF_6$ microbubbles were obtained as described in Example 5. The microbubble layer was suspended at different bubble concentrations in 0.9% NaCl, then frozen at −18° C., stored for about 4 months and thawed at room temperature.

TABLE 5

| Bubble concentration (× $10^8$/ml) | | Bubble volume (µl/ml) | | Bubble diameter (µm) | |
|---|---|---|---|---|---|
| native | freeze/thaw | native | freeze/thaw | native | freeze thaw |
| 1.9 | 1.9 (1.9)* | 6.8 | 6.0 (5.5)* | 3.1 | 3.0 (2.9)* |
| 3.9 | 3.7 (3.3) | 14.7 | 11.5 (9.4) | 3.1 | 2.8 (2.6) |
| 5.9 | 5.7 (5.4) | 22.6 | 20.4 (18.6) | 3.1 | 3.0 (3.0) |
| 7.7 | 7.6 (6.1) | 28.3 | 24.6 (17.0) | 3.0 | 2.9 (2.7) |

*in parenthesis, results obtained after a second freeze/thaw treatment

The results gathered in Table 5 show no significant effect of the bubble concentration on the resistance to freeze/thaw. Even a second freeze/thaw treatment which was performed after the storage did not effect the final concentration, showing that these suspensions are resistant to repeated freeze and thaw cycles even after storage without great loss in the bubble count and damage to the echogenicity of the samples.

EXAMPLE 7

Sonicated albumin microspheres were prepared using the method described in EP-A-0 324 928 (Widder). Briefly, 5 ml of a sterile 5% human albumin solution (from the Blood Transfusion Service of the Swiss Red Cross, Bern Switzerland) were introduced in a 10 ml calibrated syringe. A sonicator probe (Model 250 from Branson Ultrasonic Corp. USA) was lowered into the solution down to the 4 ml mark. Sonication was carried out for 30 sec at an energy setting of 7. Then the sonicator probe was raised up to the 6 ml mark (i.e. above the solution level) and sonication was pursued in the pulse mode (0.3 s/cyde) for 40 seconds. After removal of a foam layer, a suspension of albumin microspheres was obtained containing $1.5 \times 10^8$ bubbles per ml with a number mean diameter of 3.6 µm. This suspension was frozen at −18° and left at this temperature overnight. The day after the suspension was thawed at room temperature. The suspension analysed before and after freeze/thawing had the following characteristics:

TABLE 6

| Sample (with air) | Absorbance 700 nm | Bubble conc. (× $10^8$/ml) | Diameter Dn (µm) |
|---|---|---|---|
| native | 0.25 | 1.4 | 3.6 |
| after freeze/thaw | 0.13 | 0.4 | 6.3 |

The results in Table 6 show certain degree of destruction of the air containing microbubbles by freezing and defrosting cycle. When instead of pure air the albumin microbubbles are prepared with mixtures of air containing about 5% by vol. of $C_5F_{12}$ or $C_3F_8$, the stability of the microspheres against freeze/thaw loss of bubble count was greatly improved (see Table 7). From the results obtained with albumin microspheres it can also be seen that freeze/thaw cycles in case of air microbubbles are detrimental for the lower end of sizes of the microbubble population i.e. that the microbubbles with average size of about 5 µm or more have better resistance and chance of survival than the smaller microbubbles.

TABLE 7

| Sample (air + 5% $C_5F_{12}$) | Absorbance 700 nm | Bubble conc (× $10^8$/ml) | Diameter Dn (µm) |
|---|---|---|---|
| native | 0.64 | 2.4 | 3.7 |
| after freeze/thaw | 0.39 | 1.1 | 4.3 |

EXAMPLE 8

When 3 g of saccharide micropartides SHU-454, a commercial echo contrast agent (Echovist®, Schering, Germany) were reconstituted in a galactose solution (8.5 ml, 200 mg/ml) as recommended by the manufacturer and submitted to a freeze/thaw treatment, only few bubbles were present in the solution after thawing. If 10 mg per ml of a mixture of dipalmitoylphosphatidylglycerol and Pluronic® $F_{68}$ (1:5, w:w) were added to the galactose solution prior to the addition of the saccharide microparticles, stable microbubbles could be obtained at a concentration of $2.5 \times 10^8$ bubbles per ml. After freezing and thawing the bubble concentration dropped, about three orders of magnitude, to $2.3 \times 10^5$ per ml indicating a considerable loss of microbubbles during the treatment. However if prior to reconstitution, air in the gas phase was replaced by a mixture of air containing 10% $C_5F_{12}$, the bubbles were more stable and also more resistant to a freeze/thaw treatment. The loss of microbubbles in the later case was only $2.3 \times 10^8$ as the concentration dropped from $3.9 \times 10^8$ to $1.6 \times 10^8$ bubbles per ml.

EXAMPLE 9

Polymeric microballoons were prepared using the technique described in Example 4 of EP-A-0 458 745 (Bracco International). The polymer used in this preparation was poly-POMEG which is described in U.S. Pat. No. 4,888,398.

The microballoons were suspended at a concentration of $1.8 \times 10^8$ particles per ml in distilled water, 0.9% NaCl, 5% dextrose, and 3% glycerol. Each of these suspensions was frozen then thawed. No detectable change was observed after thawing, neither on the total particle concentration, nor on the mean particle diameter.

EXAMPLE 10

Figure 1:
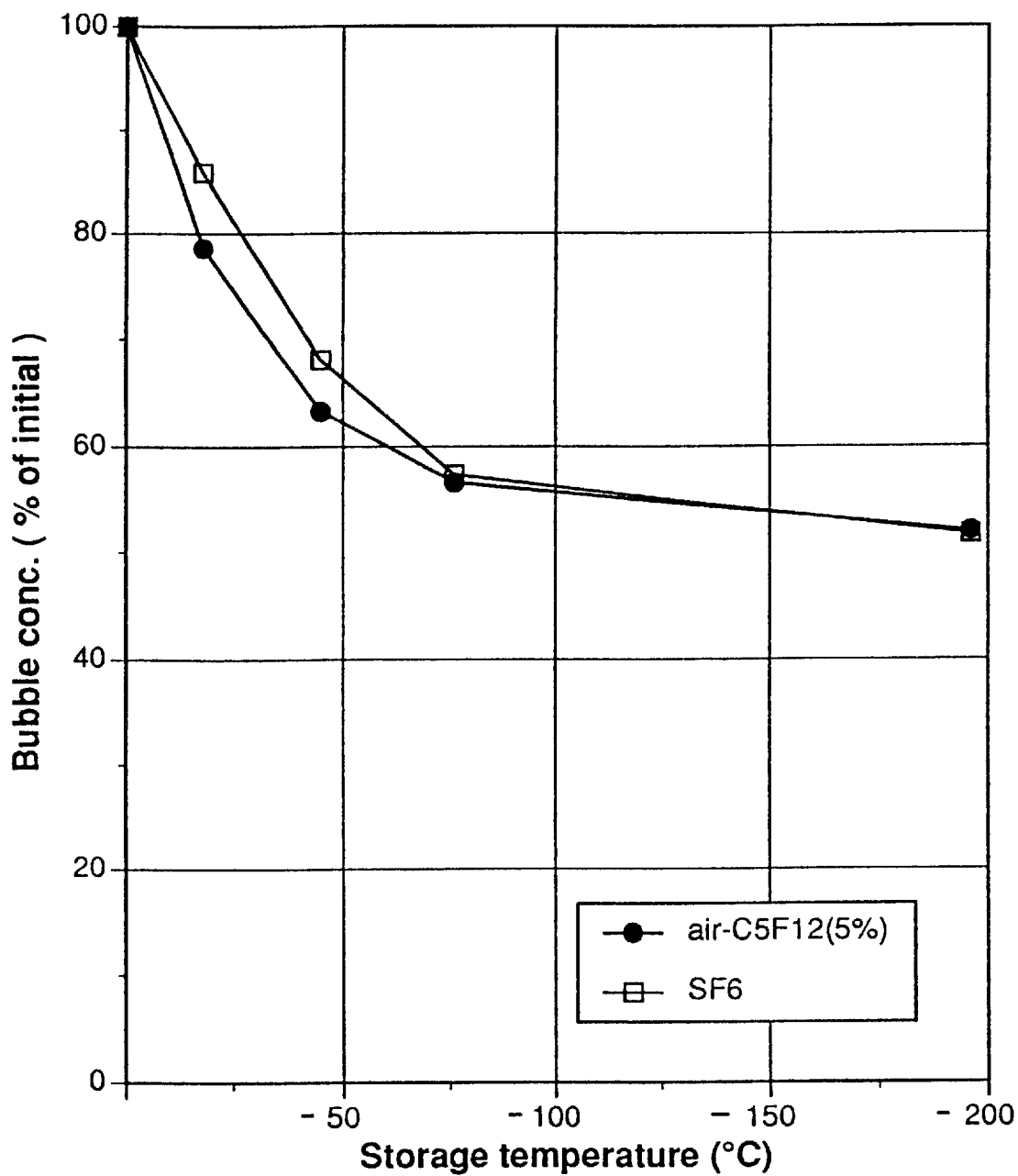
FIG. 1 is a plot of change in the bubble concentration (count) in defrosted suspensions of $SF_6$ and air containing 5% of $C_5F_{12}$ microbubbles in an aqueous carrier medium as a function of storage temperature.
Figure 2:
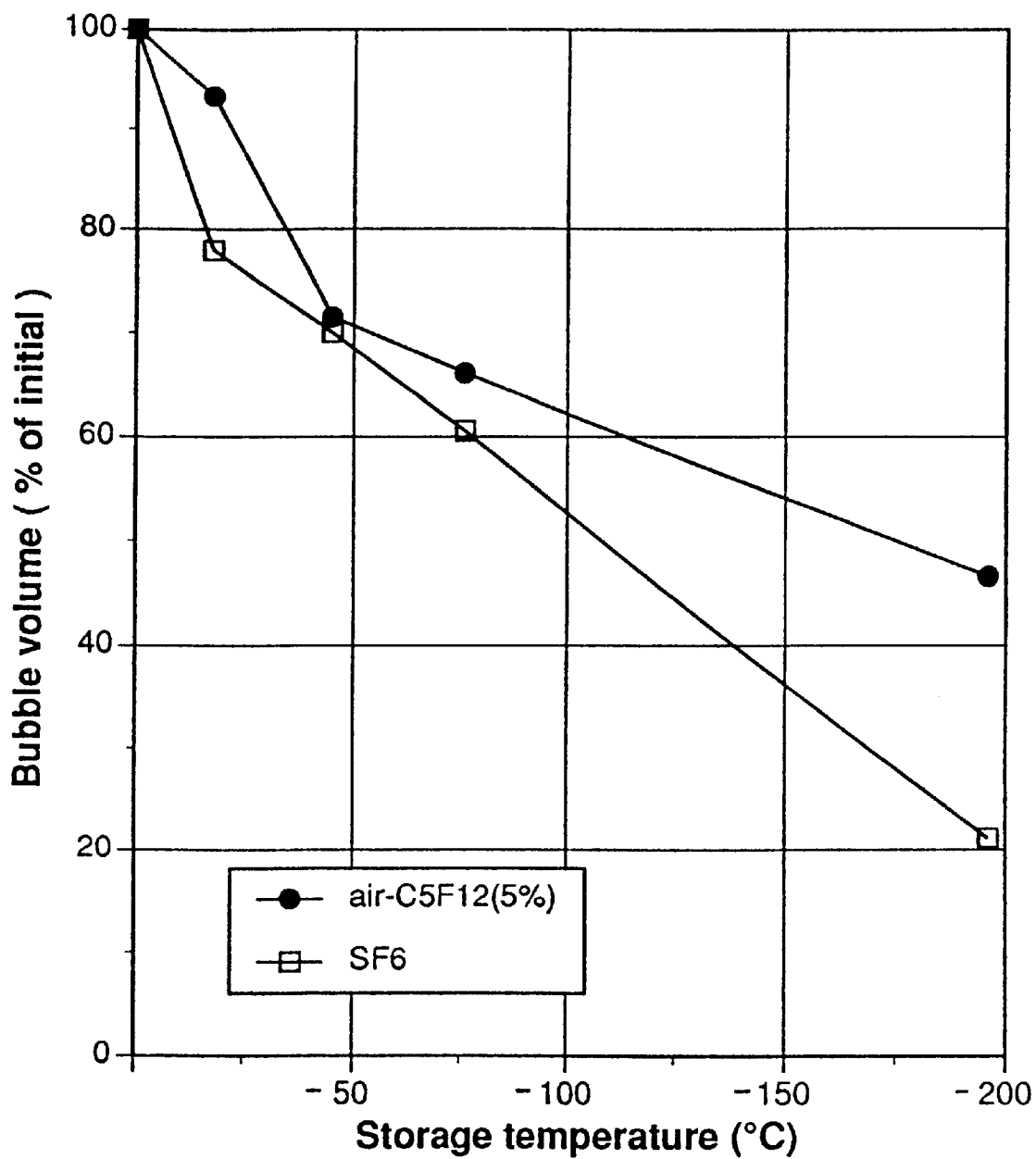
FIG. 2 is a plot of change in the total gas volume of defrosted suspensions of $SF_6$ and air containing 5% $C_5F_{12}$ microbubbles in an aqueous carrier medium as a function of storage temperature.

A quantity of 126 mg of egg lecithin and 27 mg of cholesterol were dissolved in 9 ml of diethylether in a 200 ml round bottom flask. To the solution were added 3 ml of 0.2 molar aqueous solution of sodium bicarbonate with ionophore A23187 and the resulting two phase system sonicated until becoming homogeneous. The mixture was air/5% $C_5F_{12}$ mixture there is a relatively small change in the microbubble diameter. Results also show that the average microbubble diameter decreases with decrease in the storage temperature. As shown in FIG. 1 for suspensions with $SF_6$ and air/$C_5F_{12}$ mixture only 51.7% and 52% of the initial microbubble population is recovered after storage at $-196°$ C. However, as seen from FIG. 2 the total gas volume recovered after the storage for $SF_6$ is 21.1% of the initial volume while for air/$C_5F_{12}$ mixture the volume recovered is 46.5%. This indicates that the size of microbubbles in the case of suspensions prepared with $SF_6$ has changed, i.e. that the microbubbles recovered have reduced diameters.

TABLE 8

| Gas | Gas volume recov. $\mu$l/ml | Diam Dn after thaw | Bubble conc. × $10^7$ recov | Temp. ° C. | Gas mixture air with 5% $C_5F_{12}$ | Gas volume recov. $\mu$l/ml | Diam Dn after thaw | Bubble conc. × $10^7$ recov |
|---|---|---|---|---|---|---|---|---|
| $SF_6$ | 2.3 | 2.4 | 10.0 | −18 | air/$C_5F_{12}$ | 5.5 | 4.6 | 7.7 |
| $SF_6$ | 2.8 | 2.6 | 7.9 | −45 | air/$C_5F_{12}$ | 4.2 | 4.5 | 6.2 |
| $SF_6$ | 1.8 | 2.5 | 6.7 | −70 | air/$C_5F_{12}$ | 3.9 | 4.4 | 5.6 |
| $SF_6$ | 0.6 | 2.0 | 6.0 | −196 | air/$C_5F_{12}$ | 2.7 | 4.0 | 5.1 | evaporated to dryness on a Rotavapor and a 3 ml of a 0.2 molar aqueous bicarbonate solution were added to the flask containing the lipid deposit.

After standing for a while, the resulting liposome suspension was dialysed against saline to eliminate non-entrapped bicarbonate and acidified. After a while it was washed with distilled water and then passed several times through a cascade of carbonate filters. An aliquot of the suspension of liposomes with size below 50 $\mu$m was then frozen at $-18°$ and stored at this temperature. Two weeks later the suspension was thawed at room temperature. The suspension analysed before and after freeze/thawing showed an acceptably low loss of echogenicity and microbubble count.

EXAMPLE 11

Procedure of the Example 3 was repeated using $SF_6$ and air containing 5% $C_5F_{12}$ as the gas phase and the samples of the resulting suspension were frozen at $-18°$ C., $-45°$ C., $-76°$ C. and $-196°$ C. After thirty days of storage at the corresponding freezing temperatures the samples were defrosted and suspensions analysed. The results obtained are presented in Table 8. The concentration of microbubbles in the samples before freezing was $11.6 \times 10^7$/ml for $SF_6$ and $9.8 \times 10^7$/ml for the air/5% $C_5F_{12}$ mixture while the respective volumes of gases in the samples prior to storing were 2.9 $\mu$l/ml and 5.9 $\mu$l/ml. The average microbubble diameter for the two gases was 2.3 $\mu$m and 4.2 $\mu$m.

Figure 3:
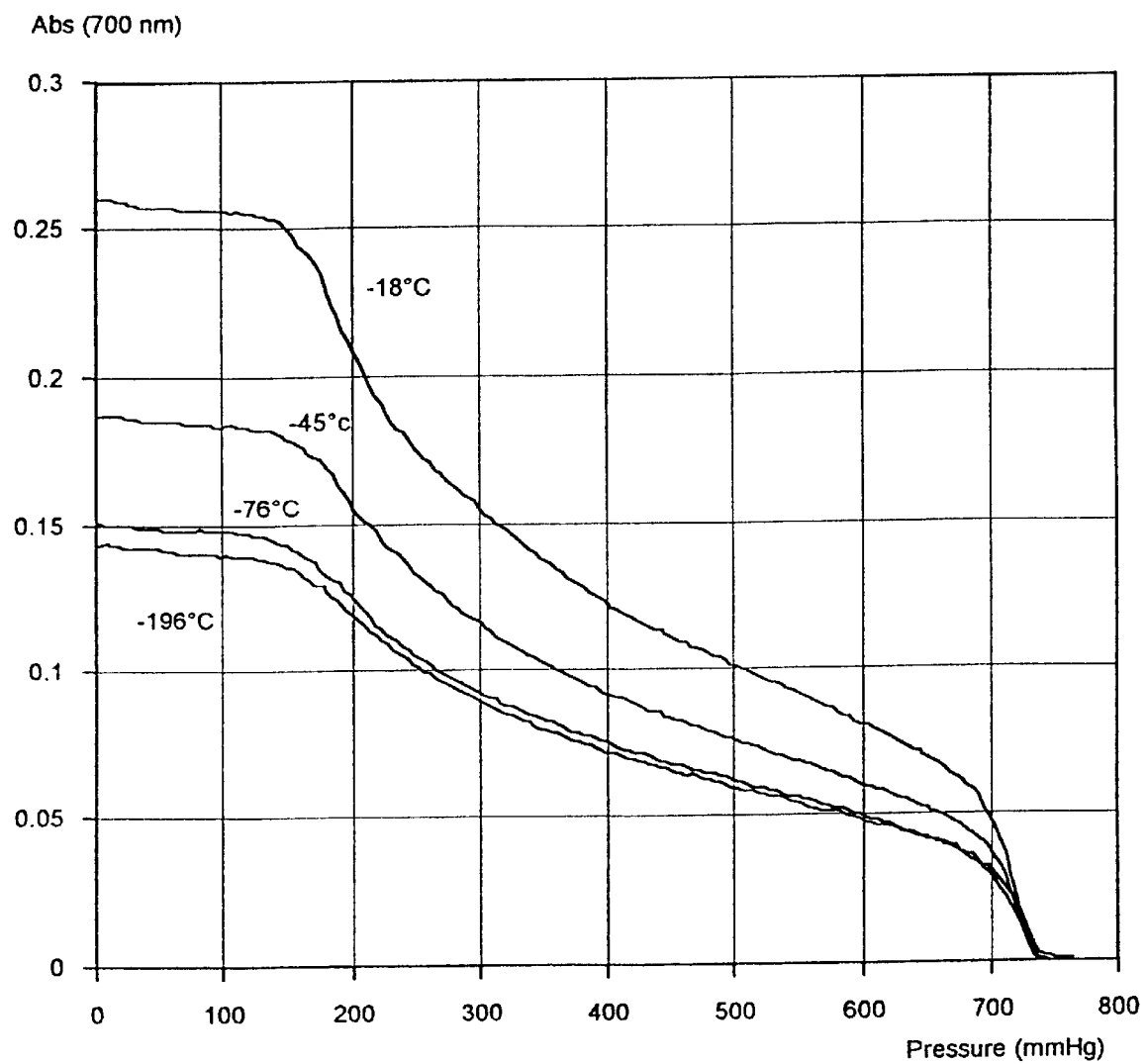
FIG. 3 is a graphical presentation of change in absorbance of defrosted microbubble suspensions as a function of external pressure applied and storage temperature.
Figure 4:
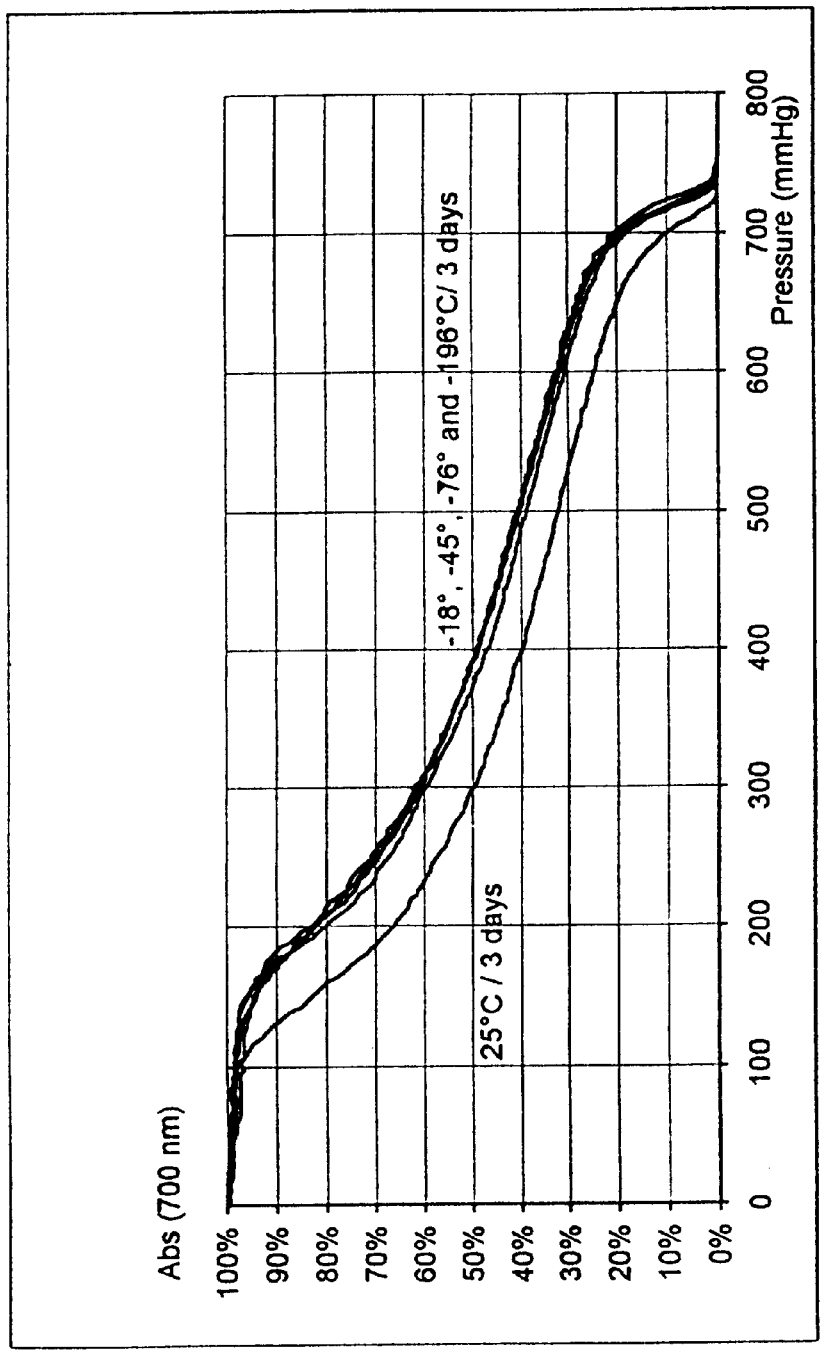
FIG. 4 is a diagram showing change of relative absorbance as a function of external pressure applied to defrosted suspensions after storage at different temperatures.

From the results it follows that the lower the temperature of storage the greater loss in the microbubble concentration and the total amount of gas recovered upon defrosting. The results further show that for defrosted samples of suspensions with $SF_6$ the average diameter at first increases and then as the temperature is lowered sharply decreases. For the FIG. 3 and 4 illustrate the effect of freezing or storage temperature on the resistance to pressure change of suspensions of microbubbles containing a mixture of air with 5% $C_5F_{12}$. In the diagram in FIG. 3 absorbance (measured at 700 nm) is presented as a function of pressure applied onto suspensions after storage for three days at different temperatures. From this diagram it follows that the decrease in the storage temperature has an impact on the properties of the suspensions such that the change in properties of the suspensions stored at temperatures between $-18°$ C. and $-76°$ C. is significant while the change for the samples stored between $-76°$ C. and $-196°$ C. is relatively small. Thus maintaining storage temperatures below $-76°$ C. does not seem to provide further advantages. In view of the costs involved chosing temperatures below $-76°$ C. may be justified only in exceptional cases.

FIG. 4 on the other hand shows that if suspensions of microbubbles containing air/5% of $C_5F_{12}$ mixture are stored for three days at low temperatures their resistance to pressure variation remains relatively unchanged while the same suspension kept during the same period at 25° C. loses about 10% of its initial resistance to pressure variations.

The exact procedure and importance of critical pressure and the absorbance measurement has already been explained in EP-A-0 554 213 incorporated herein by reference.

EXAMPLE 12

Two-dimensional echocardiography was performed using an ACUSON 128 XP 5 equipment (Acuson Corp. USA) with the preparations of Example 1, 3 and 7 in experimental minipigs following peripheral vein injection of 0.04 ml/kg body weight. Left ventricle echo contrast enhancement was assessed in the case of native as well as frozen/thawed samples. No significant differences were noticed even in the cases of samples such as the ones described in Example 7 for albumin microspheres, indicating that the residual bubbles were largely sufficient to produce a strong and long lasting echo enhancement.

We claim:

1. A frozen suspension of halogen-containing, gas bubbles immobilized within a frozen aqueous carrier medium at a temperature between −1° C. and −196° C., wherein the carrier medium comprising the gas bubbles is a physiologically acceptable carrier, the immobilized halogen-containing gas bubbles are microbubbles bounded by an evanescent surfactant gas/liquid envelope or a tangible, water-insoluble non-proteinaceous membrane, the encapsulated microbubbles below 10 μm in size, the suspension, when in liquid form, being injectable and useful as a contrast agent in ultrasonic imaging of blood pool and tissue of living beings.

2. The suspension of claim 1, wherein the temperature of the frozen medium is between −10° C. and −76° C.

3. The suspension of claim 1, wherein the size of most of the microbubbles is below 10 μm.

4. The suspension of claim 1, wherein the size of the microbubbles is between 2 μm and 9 μm.

5. The suspension of claim 4, wherein the size of the microbubbles is between 3 μm and 5 μm.

6. The suspension of claim 1, wherein the evanescent envelope or tangible membrane bounding the microbubbles is a surfactant or a lamellar phospholipid in the form of mono- or pluri-molecular membrane layers.

7. The suspension of claim 6, wherein the lamellar phospholipids are in the form of unilamellar or multilamellar liposomes.

8. The suspension of claim 6, wherein the lamellar phospholipids are saturated phospholipids.

9. The suspension of claim 7, wherein the phospholipids are selected from phosphatidic acid, phosphatidylcholine, phosphatidylethanolamine, phosphatidylserine, phosphatidylglycerol, phosphatidylinositol, cardiolipin and sphingomyelin or mixtures thereof.

10. The suspension of claim 1, wherein the carrier medium includes at least one additive selected from dicetylphosphate, cholesterol, ergosterol, phytosterol, sitosterol, lanosterol, tocopherol, propyl gallate, ascorbyl palmitate and butylated hydroxytoluene.

11. The suspension of claim 1, wherein the carrier medium includes sorbitol or polyoxyethylene/polyoxypropylene copolymers.

12. The suspension of claim 1 wherein the carrier medium includes a viscosity enhancer or stabilizer selected from linear and cross-linked poly- and oligo-saccharides, sugars, hydrophilic polymers and iodinated compounds in a weight ratio to the surfactants comprised between about 1:5 and 100:1.

13. The suspension of claim 6 wherein the additives further comprise up to 50% by weight of a non-laminar surfactant selected from fatty acids, esters and ethers of fatty acids and alcohols with polyols.

14. The suspension of claim 13 wherein the polyols are polyalkylene glycols, polyalkylenated sugars and polyalkylenated glycerol.

15. The suspension of claim 1, containing $10^8$–$10^8$ microbubbles/ml, $10^8$–$10^9$ microbubbles/ml or $10^9$–$10^{10}$ microbubbles/ml.

16. The suspension of claim 1, containing $10^8$–$10^9$ microbubbles/ml.

17. The suspension of claim 1, containing $10^9$–$10^{10}$ microbubbles/ml.

18. The suspension of claim 1, wherein the membrane is made of synthetic or natural polymer.

19. The suspension of claim 18, wherein the polymer is selected from polysaccharides, polylactides and polyglycolides and their copolymers, copolymers of lactides and lactones, poly-(ortho)esters, polydioxanone, poly-β-aminoketones, polyphosphaze-nes, polyanydrides, polyalkyl-(cyano)-acrylates, polyolefins, polyacrylates, polyacrylonitrile, non-hydrolyzable polyesters, polyurethanes and poly-ureas.

20. The suspension of claim 1, wherein the halogen-containing gas is selected from the group consisting of $SF_6$, $CF_4$, $C_2F_6$, $C_3F_6$, $C_3F_8$, $C_4F_6$, $C_4F_8$, $C_4F_{10}$, $C_5F_{10}$, $C_5F_{12}$ and mixtures thereof.

21. An injectable suspension of claim 1 for use in ultrasonic imaging of organs and tissue.

* * * * *